(12) United States Patent
Rousseau

(10) Patent No.: US 8,636,810 B2
(45) Date of Patent: Jan. 28, 2014

(54) NEGATIVE PRESSURE INTESTINAL ANASTOMOSIS PROTECTION DEVICES

(75) Inventor: Robert Anthony Rousseau, Ottsville, PA (US)

(73) Assignee: Ethicon, Inc., Somerville, NJ (US)

( * ) Notice: Subject to any disclaimer, the term of this patent is extended or adjusted under 35 U.S.C. 154(b) by 152 days.

(21) Appl. No.: 13/246,924

(22) Filed: Sep. 28, 2011

(65) Prior Publication Data

US 2013/0079890 A1  Mar. 28, 2013

(51) Int. Cl.
*A61F 2/04* (2013.01)
*A61B 17/08* (2006.01)

(52) U.S. Cl.
USPC ............... 623/23.68; 623/23.64; 623/23.65; 606/151; 606/153; 606/155

(58) Field of Classification Search
USPC .............. 623/23.64, 23.65, 23.68, 1.35, 1.24, 623/1.26, 1.27, 1.3; 137/844, 845
See application file for complete search history.

(56) References Cited

U.S. PATENT DOCUMENTS

| | | | |
|---|---|---|---|
| 4,641,653 A | | 2/1987 | Rockey |
| 4,721,109 A | * | 1/1988 | Healey ........................ 606/156 |
| 5,156,620 A | | 10/1992 | Pigott |
| 5,180,392 A | * | 1/1993 | Skeie et al. ................ 623/23.64 |
| 7,122,058 B2 | * | 10/2006 | Levine et al. .............. 623/23.65 |
| 7,211,114 B2 | | 5/2007 | Bessler |
| 2004/0039452 A1 | | 2/2004 | Bessler |
| 2004/0093026 A1 | | 5/2004 | Weidenhagen |
| 2005/0273060 A1 | | 12/2005 | Levy et al. |
| 2009/0093837 A1 | | 4/2009 | Dillon |

FOREIGN PATENT DOCUMENTS

| | | |
|---|---|---|
| WO | 03/037222 | 5/2003 |
| WO | 2006/071707 | 7/2006 |

* cited by examiner

*Primary Examiner* — Thomas J Sweet
*Assistant Examiner* — Krutanjali M Shah
(74) *Attorney, Agent, or Firm* — E. Richard Skula

(57) ABSTRACT

A device is disclosed that provides for the protection of intestinal anastomosis sites and other body sites from bodily fluids and contaminants. Additionally, the device provides the ability to create negative pressure at the site of the obstruction to ensure that contaminants flow from the visceral compartment into the inner lumen of the bowel. Further, the device provides the sectional forces through natural constrictions of the intestinal muscles through peristaltic action.

35 Claims, 7 Drawing Sheets

NEGATIVE PRESSURE INTESTINAL ANASTOMOSIS PROTECTION DEVICES

FIELD OF THE INVENTION

The field of art to which this invention pertains is medical devices, more specifically, medical devices for protecting tissue sites against contamination.

BACKGROUND OF THE INVENTION

There are a host of intra-abdominal and intra-thoracic sites in which abscesses may occur. In certain endoscopic procedures, such as anterior resection of the rectum, complications may occur leading to anastomotic leakage, which in turn may lead to an abscess formation. Some studies have shown that anastomotic leakage after anterior resection of the rectum occurs anywhere from 4.5% to 18% of the time. Such problems are often aggravated by a physiologic obstruction in the anal region. Accumulation of gases and feces results in movement of this waste material through the path of least resistance, which in most cases, and especially in the case of anastomotic leakage, is out of the colonic lumen and into the abdominal cavity. The backflow into the abdominal cavity typically leads to a pressure build-up next to the anastomosis, which in turn leads to mechanical enlargement of the tissue at the anastomosis and formation of an abscess. Proper healing of the anastomosis is therefore continually impaired.

During healing, the materials that are utilized to reattach the tissues are in direct contact with intestinal contaminants. These contaminants may enter into the walls of the intestinal repair through this contact with the stool and other contaminants, depending upon the location of the repair. This contamination of the site may contribute to serious complications including delayed healing, increased risk of infection or tissue necrosis, and anastomosis repair leakage.

Negative pressure therapy has been utilized for the healing of open wounds and has been commercialized, for example, by Kinetic Concepts, Inc. of San Antonio, Tex., with its proprietary V.A.C.® product line. In practice, the application to a wound of negative gauge pressure, typically involves the mechanical-like contraction of the wound with simultaneous removal of excess fluid. In this manner, V.A.C.® therapy augments the body's natural inflammatory process while alleviating many of the known intrinsic side effects, such as the production of edema caused by increased blood flow absent the necessary vascular structure for proper venous return. As a result, V.A.C.® therapy has been shown to be highly successful in the promotion of wound closure, healing many wounds previously thought largely untreatable. However, treatment utilizing V.A.C.® therapy has been largely limited to open surface wounds. Treatment of internal wounds, such as internal abscesses, has typically involved more traditional techniques such as surgical excision, treatment with antibiotics, etc. Other more complicated internal conditions, such as anastomotic leakage, have been even more problematic to treat.

Little has been known about the best ways to treat such anastomotic leakage. Some standard procedures used for this indication include nasogastric suction, broad-spectrum antibiotics, and parenteral nutrition. Other surgical procedures have included drainage of the leakage, loop colostomy, resection of the anastomosis (known as the Hartmann's procedure to those skilled in the art), and abdominoperineal excision of the rectum with a terminal stoma.

Products have been developed to provide temporary barriers to contaminants through the application of sleeve-like products, such as COLOSHIELD®, which are placed within the lumen of the intestinal structure and are attached superior to the anastomosis though the use of surgical sutures, staples, hooks, etc. The product is essentially a hollow tubular barrier material that is long enough to bridge the anastomosis. The barrier material serves as a physical protection against any direct contact of contaminants with the underlying healing tissue. While this product may isolate the healing tissue from pressurization by direct contact with the intestinal contaminants, the device does not provide any extraction of fluids or contaminants from the wound site. Additionally, the fixation of the device requires the use of elements that penetrate the protective barrier and are fixed within the tissues. Contaminants may infiltrate the punctures created by any of the previously-mentioned attachment devices to fixate the product.

Others in the prior art have also attempted to address this problem. For example, US 2004/0093026 discloses a negative pressure wound care treatment system including a collecting subsystem having fluid channels, which also serves as a pressure distributor and that may be comprised of an open-cell, polyurethane foam having a pore size in the range of about 400 to 600 microns. The foam may be cut to a size corresponding to the geometry of an anastomotic leakage and its corresponding cavity, which may range from 7.0 cm in length and 3.0 cm in diameter to 0.5 cm×1.0 cm. Also disclosed is a system for placing the foam within the cavity. An evacuation tube comprises at least one port that communicates with the foam and is positioned at the distal end of the tube or on a side proximate to the distal end of the tube. The distal end of the evacuation tube is preferably placed in the middle of the foam. The foam may be fixed to the tube using a non-absorbable surgical suture. Alternatively, the foam may be welded or glued to the tube using techniques known to those skilled in the art. Other alternative embodiments disclosed include the use of biodegradable foam, in which case the foam is fixed to the evacuation tube using biodegradable means, such as bioabsorbable sutures. The opposing, or proximal, end of the tube is connected to a high-vacuum drainage system, into which effluent fluid may be collected. A subatmospheric pressure of up to 850 mbar is applied to the foam. The open-cell nature of the foam apparently provides equal distribution of the applied pressure to every surface of the cavity in contact with the foam, thus serving as a pressure distributor.

U.S. Pat. No. 4,641,653 discloses a device that provides a method and means for isolating the internal walls of hollow viscera or other body vessels from contact with materials, both fluids and solids, occurring naturally, ingested, or otherwise introduced into a body vessel. Isolation of a body vessel, according to the invention, is achieved by positioning and anchoring a sleeve, impervious to materials sought to be isolated within the vessel, in such a manner that the sleeve, at least adjacent its upstream end, is in sealing engagement with the surrounding interior tissue of the vessel. Material otherwise normally flowing into the vessel and being capable of interacting with the vessel to the detriment of the patient's health is thereby contained and rendered ineffectual or otherwise unaffected by the vessel. The device may be attached to a source of pressure to deploy the sleeve against the walls of the lumen to be protected. This device simply isolates the walls of the lumen from the contaminants, and does not actively evacuate materials from the surrounding tissues.

U.S. Pat. No. 7,211,114 discloses a device that is inserted into a patient's stomach endoscopically to separate ingested food from gastric fluids and, optionally, to separate ingested food in the duodenum from digestive enzymes. In one embodiment of the invention, a stent is inserted into a patient's gastrointestinal tract to bypass the stomach. The stent consists of a covered stent having one-way openings and/or valves on its annular surface and preferably at least one one-way valve at one end to permit entry of food and/or liquids. Optionally the one-way valve at the end of the stent can comprise a sleeve that extends through the stent, preferably into the duodenum or beyond. One end of the stent is intended to be positioned at or above the gastro-esophageal junction, and the other end is intended to be positioned in the duodenum or beyond. The net effect of endoscopic gastric bypass is to replicate some or all of the effects of a surgical gastric bypass. The device as disclosed provides a means by which to isolate the digestive secretions from the food, however, it does not disclose or contemplate protecting a surgical anastomosis.

Although devices and systems are available for various wound treatment and implantation and tissue isolation applications, there is a need in this art for an endoscopic wound care treatment system that is capable of effectively treating an internal organ or tissue abscess in a minimally invasive manner, and which is easily implanted.

SUMMARY OF THE INVENTION

It is therefore an object of the present invention to provide an endoluminal wound care treatment system having an endoluminal component, that provides a means for introducing the endoluminal component, which is preferably a passive negative pressure device, into an internal organ or tissue, and in particular into an internal wound or abscess of a human body.

A further object is to provide such a system that is capable of achieving a closed abscess in a shorter period of time than current methods allow, with less trauma to the patient than current methods, and that does not require the introduction of external sources of negative pressure.

Yet another object of the present invention is a method of treating a wound with a passive negative pressure device.

Accordingly, a novel passive negative pressure endoluminal device for protecting anastomosis sites is disclosed. The device has an inner tubular member. The inner tubular member has an inner lumen, a diameter, an outer surface, an inner surface, opposed ends, and a sidewall. The diameter of the inner tubular member varies at least partially along the length of the tubular member. The device also has an outer tubular member. The outer tubular member has an inner lumen, a length, opposed ends, an outer surface, an inner surface, and a sidewall. There is an outer shape altering member having an inner lumen. At least one valve is contained in the side wall of the inner tubular member, and at least one valve is contained in the side wall of the outer tubular member. The inner tubular member is concentrically mounted in the lumen of the outer tubular member, thereby forming a fluid-tight cavity between the inner surface of the outer member and the outer surface of the inner member. The outer shape altering member may be concentrically mounted about the outer surface of the tubular member or may be integrated into the wall thickness of the outer tubular member.

Another aspect of the present invention is a medical device for protecting an anastomosis site. The medical device has a member with a generally tubular shape having a free flowing central lumen and an external surface. The device has means for collapsing the device radially, mounted to the member, and the member has at least two concentric wall layers with a free volume section enclosed between the layers. The device has means for fluid communication from the external surface of the tubular device, through the free volume section between the wall layers of the device into the central lumen of the device. The means for fluid communication is discontinuous in an unstressed condition and is directionally controlled in a stressed condition.

Another aspect of the present invention is a method of treating an anastomosis site using one of the above-described devices. The device in preferably emplaced intraluminally in an intestine, or other hollow organ that provides contractile forces, proximate an anastomosis site in order to direct bodily fluids away from the anastomosis site. The device may be emplaced in other body sites as well.

These and other features and advantages of the present invention will become more apparent from the following description and accompanying drawings.

DETAILED DESCRIPTION OF THE INVENTION

The endoluminal devices of the present invention provide for the protection of an anastomosis site from contaminants within the digestive tract, and may have additional utilities with other body organs and at other body sites. In one of its simplest embodiments, the device consists of three coaxial functional components assembled to form a "liner" that can be placed within the lumen of the intestines and can bridge the site of the anastomosis. The device optionally incorporates the means to enable endoluminal installation and removal if so desired. Other applications for the endoluminal devices of the present invention include protection of surgical sites within the stomach, esophagus, ureters, etc.

Figure 1:
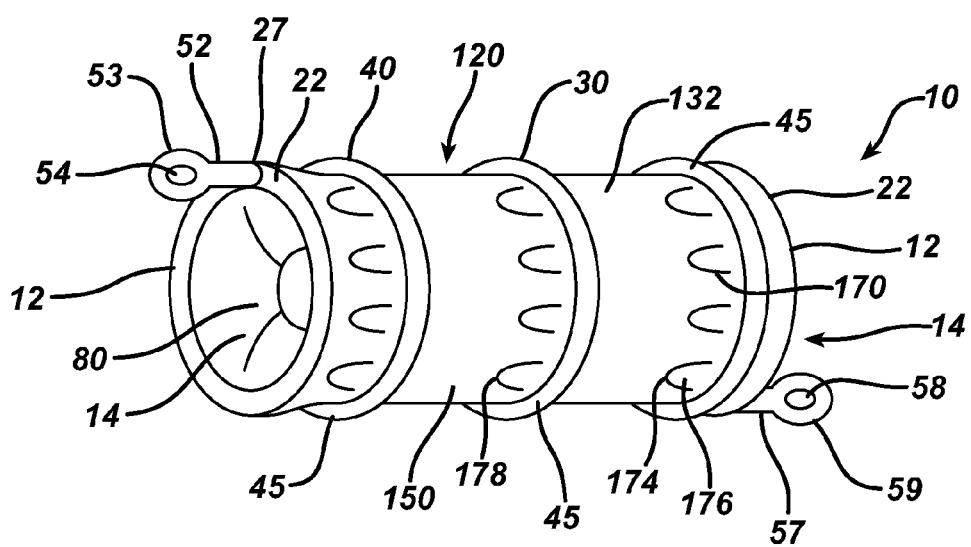
FIG. 1 is a perspective view of an assembled endoluminal device of the present invention.
Figure 2:
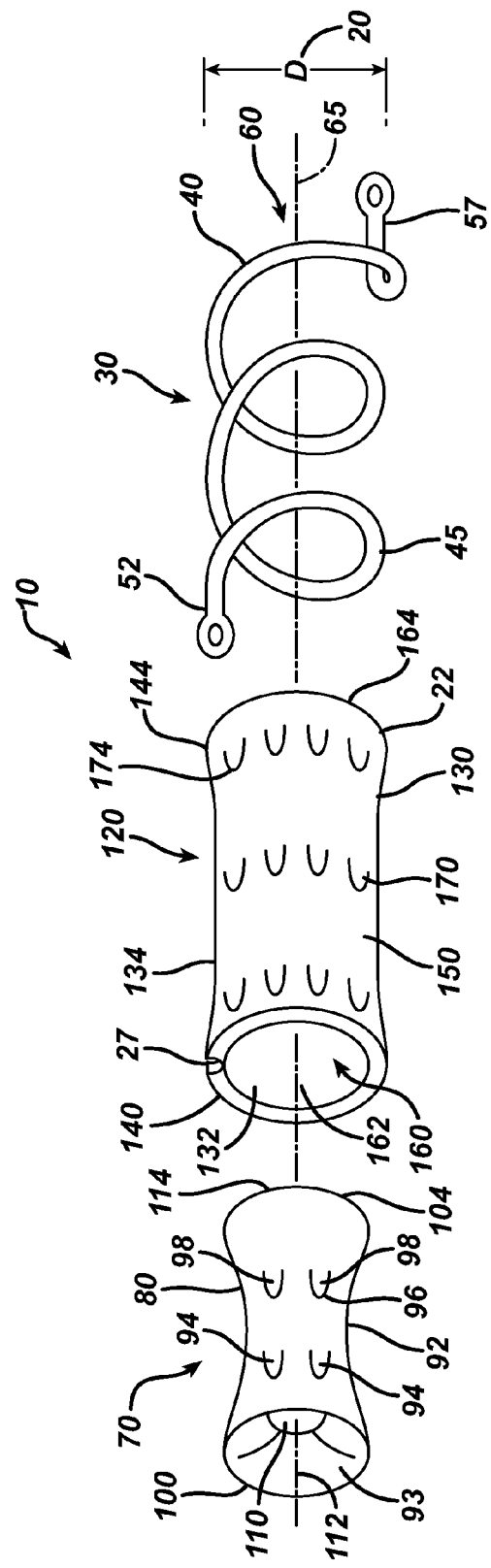
FIG. 2 is an exploded perspective view of the device of FIG. 2.

An embodiment of an endoluminal device 10 of the present invention is seen in an assembled at-rest configuration in FIG. 1, and in an exploded perspective view in FIG. 2 illustrating the components of device 10. The device 10 is seen to have opposed ends 12, and opposed end openings 14 in communication with lumen 110. The device 10 consists of three co-axial functional components; the device and components all having a longitudinal axis 65. The first or outer component 30 of the device is a compression member and is illustrated as a spiral-type winding or compression coil 40 that extends along at least part of the length of the device 10, and preferably along the entire length. The compression coil 40 is seen to have several helical loops or coils 45, and a central lumen 60. The coil 40 has a central longitudinal axis 65. Coil 40 is seen to have first end 52 and second end 57. Extending from first end 52 is the optional eyelet member 53 having passageway 54. Extending from the second end 57 is the optional eyelet member 59 having passageway 58. The eyelet members 53 and 59 are utilized to emplace or remove the device 10 in or from a lumen. Other equivalent emplacement and removal means that can be mounted to the outer component 30 include hooks, magnetic pick-ups, and the like. The coil 40 is also seen to have variable diameter D marked as reference numeral 20. This outer functional component 30 provides the means by which to collapse the entire device 10 for removal or for installation though an endoluminal approach. Compression member 30 may be made from conventional biocompatible materials including polymeric materials, composites, metals, and alloys including but not limited to surgical stainless steels and Nitinol.

In order to install or remove the device 10, the free ends 52 and 57 of the spiral component or coil 40 are engaged via eyelet member 53 and 58 with an appropriate device, such as a catheter-style device, that may provide an axial translation of the two ends 52 and 57 of the spiral 40 in opposite directions. This lengthening of the included distance will cause the spiral diameter 20 to reduce or decrease, which will collapse the underlying cylindrical components. Alternatively, the catheter device may provide rotation of the free ends 52 and 57 of the spiral member 40 about the central axis 65 of the device. The motion of the twisting of the free ends 52 and 57 is inwardly, or in the direction of the coil wind, which causes the spiral coil member 40 to collapse inwardly and to provide compression of the underlying cylindrical or tubular components. Alternatively, other functional components 30 having different configurations may be utilized in the device 10 to effectively collapse the device 10, including, for example, braided structures, or central core pulley-type arrangements that draw the central portion of the device 10 inwardly. Another alternative embodiment utilizes balloon-type structures that can be inflated to provide expansion forces and deflated to enable removal of the device 10 once the expansion force of inflation is removed. It is important to note that the outer compression member 30 should preferably be produced with a limited or interrupted tissue contact surface such as would be produced from the coil winding 40 as illustrated, a braided or foam type structure, or other textile or porous products. This allows bodily fluids and the like to flow and form pathways into the various openings in the outer surface of the device (and optionally out of the openings in the outer surface if appropriately configured).

The device 10, as illustrated in FIGS. 1-6, is also seen to have two concentric tubular or cylindrical members: an inner functional member 70 and an outer functional member 120. The members 70 and 120 may also have a variety of radial geometric cross-sections including polygonal, oval, circular, fluted, ribbed, and combinations thereof.

The second or outer functional member 120 as illustrated is a continuous tubular or cylindrical member 130. The member 130 is produced from a relatively thin-walled conventional biocompatible flexible or elastomeric material such as silicone, rubber, polyesters, urethanes, polyolefins, elastomeric thermoplastic engineering resins, elastomeric polymeric resins, and combinations thereof, etc. The member 130 is seen to have an inner surface 132, an outer surface 134, a sidewall 150, opposed ends 140 and 144, an inner passage or lumen 160, and opposed end openings 162 and 164. Openings 162 and 164 are in communication with lumen 160. The sidewall 150 is produced to have a continuous structure that is interrupted by the presence of valves 170. The particular embodiment of member 130, as illustrated, provides one-way valves 170 in the form of simple crescent-shaped cuts 174 through the sidewall 150 of the member 130 to form valve flaps 176. These cuts are made in an angular fashion and provide effectively a one-way valve mechanism. The valves 170 provide openings 178 in communication with interior lumen 160. The resilience of the member 130 is sufficient to effectively support the device 10 in position relative to a surrounding tissue luminal wall. This member 130 may alternatively be constructed as a composite layer of film and resilient members such as stents and component valves or simple flap-type valves 170 as illustrated.

The third or inner functional component 70 as illustrated is a central continuous tubular or cylindrical structure or member 80, and is produced from similar biocompatible materials to those used for component 120. Component 70 is an inner sleeve for the device 10. Tubular or cylindrical member 80 is similarly produced as a solid wall type of structure that is subsequently cut to create one way valve mechanisms. The member 80 has a sidewall 90, opposed ends 100 and 104, an inner passage or lumen 110, and opposed end openings 112 and 114. Openings 112 and 114 are in communication with lumen 110. The sidewall 90 is produced to have a continuous outer surface 92 and inner surface 93 that is interrupted by the presence of valves 94. The particular embodiment of component 70 as illustrated provides valves 94 in the form of simple crescent shaped cuts 96 through the wall 90 of the member 80 to form valve flaps 98. These cuts 96 are made in an angular fashion and provide effectively a one-way valve mechanism. The valves 94 provide openings 118 in communication with interior lumen 110. The central portion 115 of the lumen 110 is of a smaller diameter than the end regions forming effectively a hyperboloid shaped cylinder 80. The diameter of the lumen 110 may vary continuously or variably over the length of the member 80. The cylindrical member 80 is produced from materials similar to those utilized in the member 130 of device 10. The component or inner functional member 70 is produced to have an elastic radial strength that is greater than that of the outer functional member 120. Similarly to the outer member 130, the inner cylindrical member 80 may be produced as a composite structure from films and stents to provide the impervious layer.

The radial strength of inner member 80 will be greater than that of the outer member 130 in order to resist the force of peristaltic contractions of the intestinal wall to provide for compartmental compression of the volume located between the two impermeable valved layers. During peristaltic contraction, the highly flexible outer member provides minimal resistance to the peristaltic contractile forces of the intestinal walls. As a result of this flexibility, the contractile forces are transmitted to the trapped fluid volume located between the two impermeable layers. Since the inner layer provides for a greater resistance force to the contractions, the fluid volume pressure increases until the valves (or, optionally single valve) located in the inner member release to enable fluid egress from the trapped volume.

The thicknesses of the sidewalls 90 and 150 of the inner and outer tubular members 80 and 130 will be sufficient to effectively resist immediate collapse due to the radial compressive forces of peristaltic contraction. Those skilled in the art will appreciate that the thicknesses will vary with the size of the device 10, the application within the body, and the materials used to make the members 80 and 130, for example, the thicknesses may vary from about 0.006" to about 0.040". The members 80 and 130 may have the same sidewall thicknesses or different sidewall thicknesses. Similarly, the members 80 and 130 may be made from the same materials or different materials.

Figure 3A:
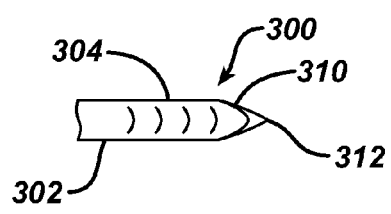
FIGS. 3A-D illustrate a cutter and its use in forming one-way crescent valves in the endoluminal devices of the present invention.
Figure 3B:
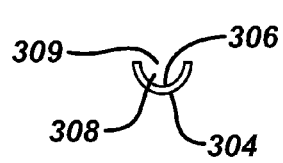
Figure 3C:
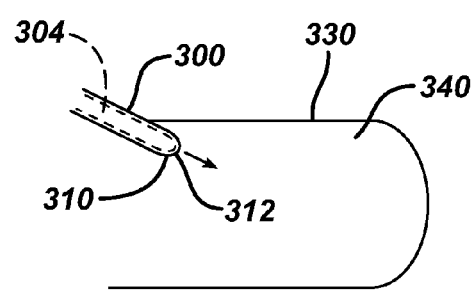
Figure 3D:
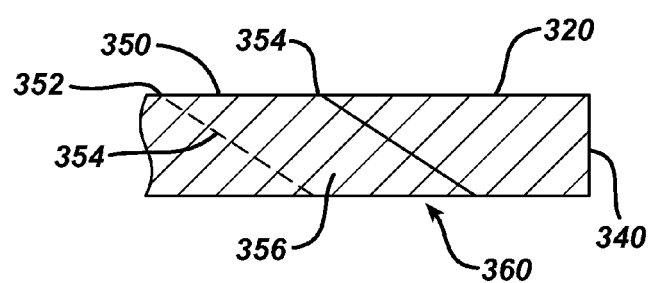

One preferred method of forming the one-way valves in the sidewalls 90 and 150 of members 80 and 130 is illustrated in FIGS. 3A-D showing a relatively simple method of producing valve cuts to form the valves. As seen in FIGS. 3A-B, a cutting instrument 300 is illustrated having a member 302 with a top side 304 and a bottom side 306. The member has a semicircular or curved cross-sectional configuration creating a channel 308 having an open side 309. The member has a distal end 310 having an extending cutting edge 312. Referring now to FIGS. 3C-D, the instrument 300 is used to make one-way valves 350 in the sidewall 340 of a tubular member 330 by pressing the distal end 310 and cutting edge 312 against the side wall 340 (at a sufficiently effective angle) to make an arcuate cut 354 in and through sidewall 340 to create a valve 350 having a valve member 356 that can pivot inwardly about living hinge section 352. When the valve member 356 pivots inwardly, it provides valve opening 360 through the side wall 340. Although slit-type valves have been described, other types of one-way valves may be incorporated into the side walls of the inner tubular member 80 and the outer tubular member 130. Such valves include conventional valves including flap, ball, balloon, piston, tricuspid and the like.

Figure 4A:
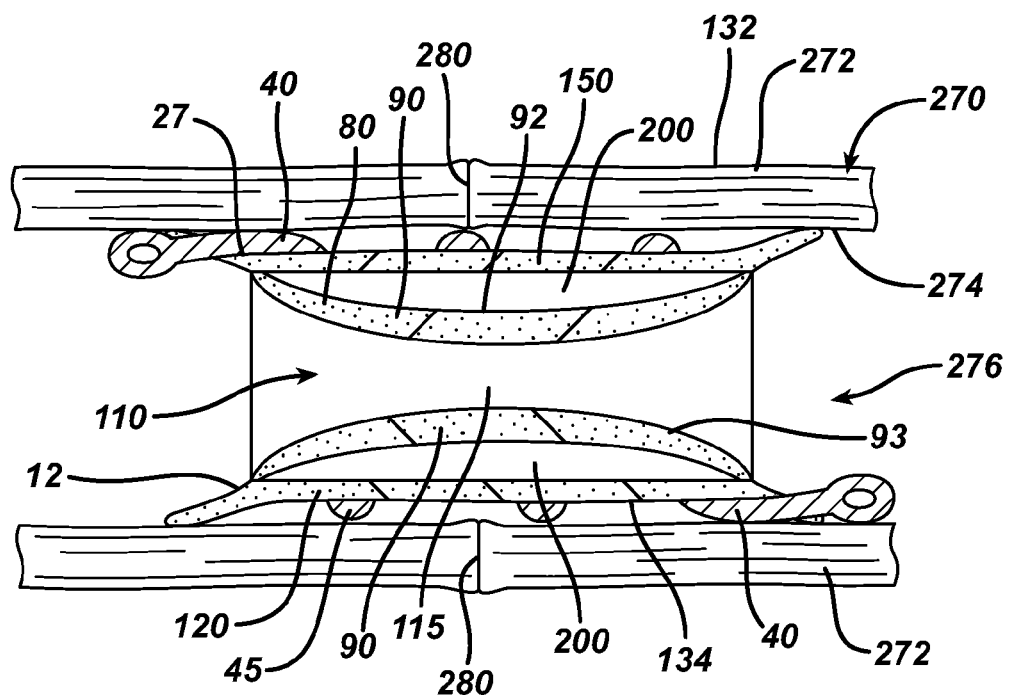
FIG. 4A is a cross-sectional view illustrating the placement of an endoluminal device of the present invention in an intestine adjacent to a surgical anastomosis.
Figure 4B:
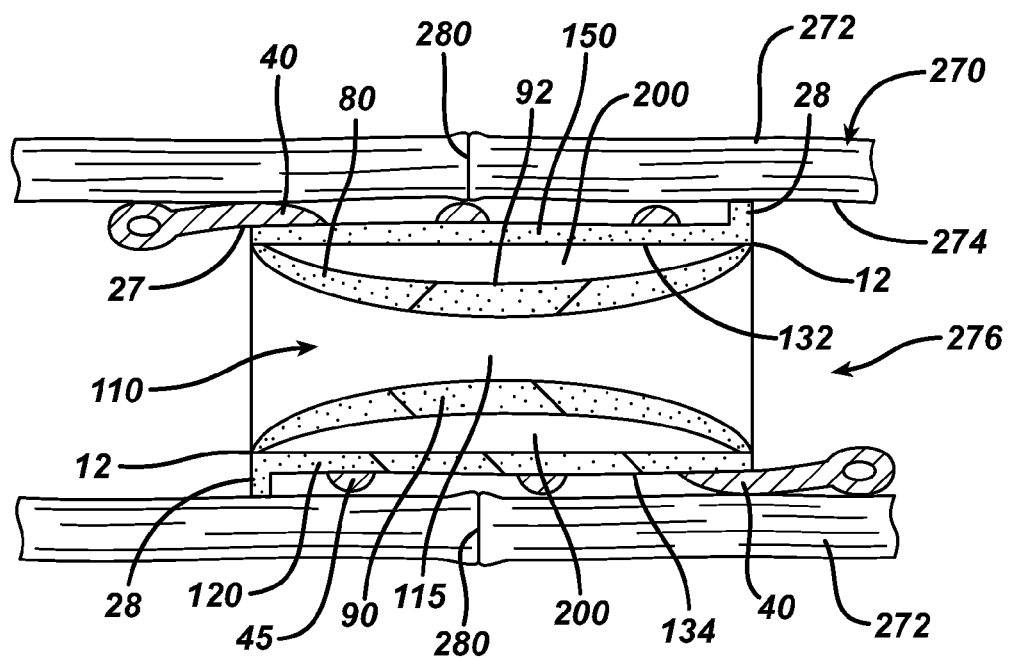
FIG. 4B is a cross-sectional view of an endoluminal device of the present invention having optional end flanges in an intestine adjacent to a surgical anastomosis.

The device 10 of the present invention is assembled in the following manner. The member 80 is concentrically mounted in the lumen 160 of tubular member 130 such that the ends 140 and 144 are coextensive with the ends 100 and 104 respectively. Although it is preferred that the ends be coextensive, optionally one or both of the ends 140 and 144 may be offset from the ends 100 and 104, e.g., the inner tubular member 80 may have a shorter length than that of member 130. The sidewalls 90 and 150 of the members 80 and 130 are bonded or connected together about their end perimeters using methods such as adhesives, thermal bonding such as welding, or mechanical bonding such as interlocking features or mechanical compression devices such as crimp collars and collets. This bonding of the end perimeters of the members 80 and 130 produces an enclosed volume or cavity 200 between the outer surface 92 of member 80 and the inner surface 132 of member 130 as seen in FIGS. 4A and B. Although as described and illustrated the cavity 200 is seen to have a continuous annular configuration, it is also within the contemplation of scope of the present invention to have the cavity 200 configured so as to have one or more pockets or compartments such that fluid flow into the device 10 is limited to such compartments or pockets. Extending about the ends 12 of the device 10 are the luminal seal members 22, one embodiment of which is seen in FIG. 4A. The seal members 22 may be formed in a variety of conventional manners, for example by extending the ends 140, 144, 110 and 104 longitudinally and radially outwardly when connecting them about their end perimeters as described above, or a separately made sealing members 22 may be mounted to the ends 12 of device 10 using conventional methods such as bonding, welding, gluing, fastening, etc. Another embodiment of a luminal seal useful with the devices 10 of the present invention is seen in FIG. 4B. The luminal seal 28 is seen to have a conventional flange-like configuration that extends from and about the ends 12 of device 10. An optional notch 27 is seen in seal members 22 and 28 to receive a section of compression member 30 when a helical coil spring 40 is utilized. Other embodiments of the compression member 30 may or may not utilize the optional notch 27. If desired, the functional members 80 and 120 may be molded as a single unitary member using conventional process such as injection molding, rather than joining or mounting the separate members 80 and 120 together as described above.

The outer compression member component 30, in this case the spring member 40, is mounted to the subassembly of members 80 and 130 in a conventional manner including adhesives, frictional engagement with the outer surface of the outer membrane, receiving features molded into the outer surface of the outer tubular member, or casting of the component within the wall thickness of the outer tubular member. This completes the assembly of the device 10. In another embodiment of the present invention (not illustrated) the compression member 30 is optionally integrated into the wall of the outer functional member 120, for example, in sidewall 150 of tubular or cylindrical member 130.

The outer functional members 70 and 120 will have a sufficient number of valves to effectively provide for the desired fluid flow. For example, a minimum of one up to forty or more may be utilized. The valve quantity will depend upon several factors including lumen diameter, device length, cavity configuration, and valve geometry including the valve opening size. The members 70 and 120 may have the same number of valves or each member may have a different number of valves and different types of valves. The openings of the valves may vary in size and configuration such that there are combinations of different sizes of valves in members 70 and 170.

Those skilled in the art will appreciate that the dimensions of the devices 10 will vary depending upon the application, the anatomic site, patient size, and the materials of construction, etc., and may vary from the ranges listed herein. For example, the devices 10 of the present invention will have a sufficient length to effectively cover beyond the clamping region of anastomosis. The devices 10 of the present invention will have a sufficient outer diameter to effectively comply with the inner luminal walls of the organ. For example, and not meant to be limiting, for endoluminal applications involving protecting and treating an intestinal anastomosis, the length of the device 10 will typically be about 2 to about 10 cm, more typically about 4 to about 8 cm, and preferably about 5 to about 6 cm. The outer diameter of the device 10, for example, will typically be about 2 to about 7 cm, more typically about 2 to about 3.5 cm, and preferably about 2.5 to about 3 cm for the small intestine. The cavities 200 of the devices 10 will have a sufficient volume to effectively maintain a negative pressure at the site of the anastomosis between the peristaltic waves. For example, and not meant to be limiting, the volume will typically be about 2 to about 16 ml, more typically about 4 to about 10 ml, and preferably about 6 to about 8 ml. The minimum inner diameter of the devices 10 of the present invention will be sufficient to effectively allow passage of intestinal contents and/or other bodily fluids. For example, and not meant to be limiting, the inner diameter will typically be about 1.5 to about 3 cm, more typically about 1.8 to about 2.5 cm, and preferably about 2 to about 2.2 cm for the small intestine.

Figure 5:
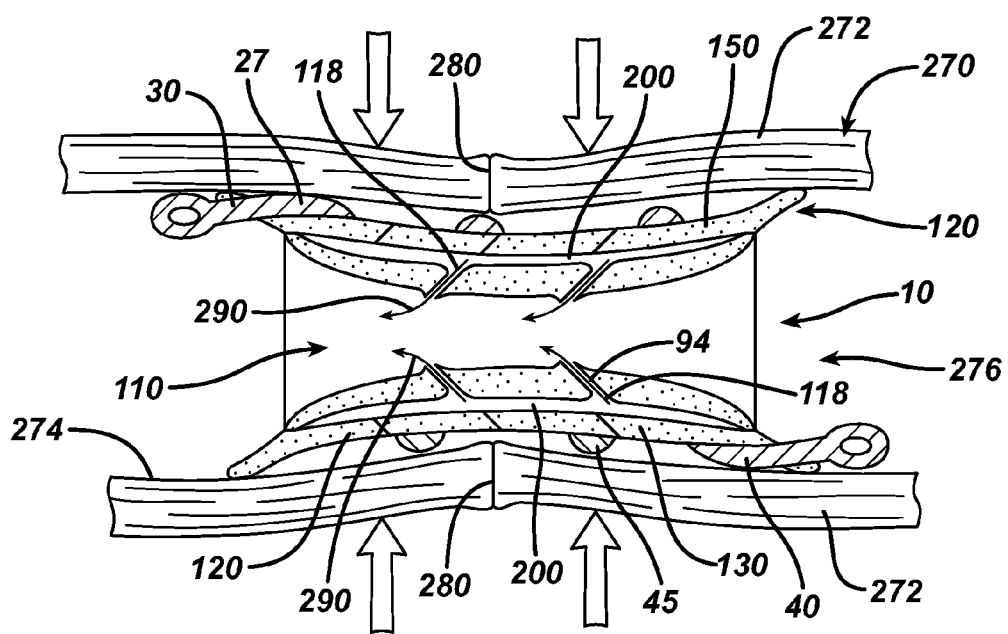
FIG. 5 is a cross-sectional view that illustrates the device of FIG. 4 in a compressed configuration induced by peristaltic contraction.
Figure 6:
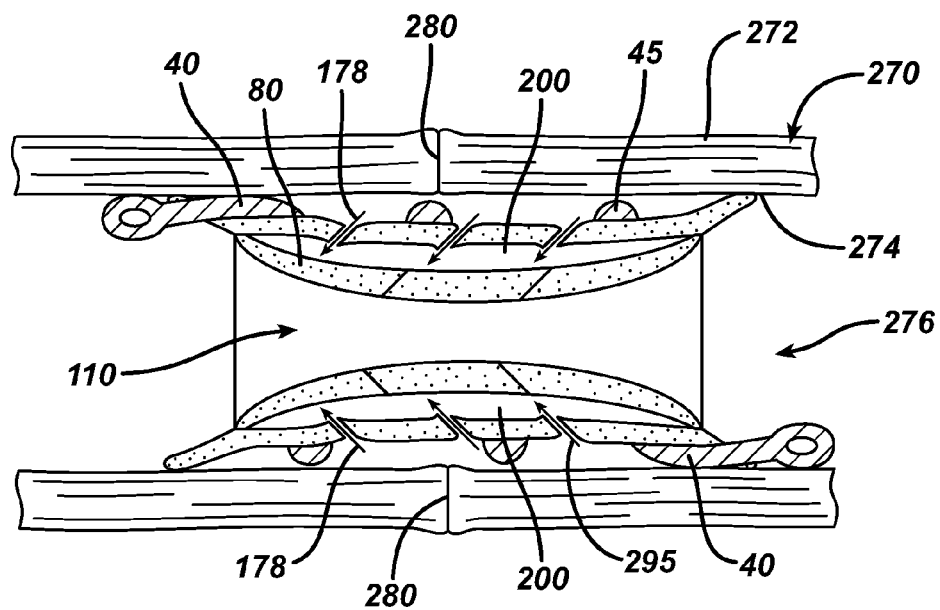
FIG. 6 is a cross-sectional view illustrating the device of FIG. 5 after the contraction has been released and the device is in an at-rest configuration.
Figure 7:
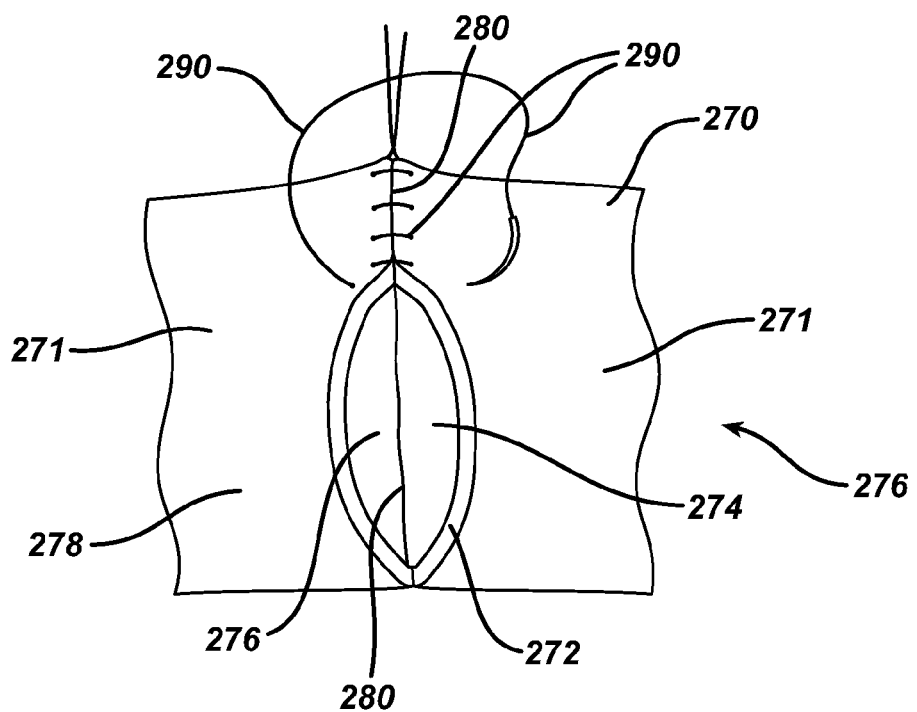
FIG. 7 is a diagrammatic illustration of an intestinal anastomosis.

The device 10 of the present invention is preferentially inserted into the site of an anastomosis at the time of surgery. A cross-section of the device 10 mounted in an intestine 270 is seen in FIGS. 4-6. A diagram illustrating an anastomosis procedure is seen in FIG. 7. The intestine 270 is seen to have a section removed with the sections of intestine 271 on either side of the anastomosis 280 joined together in a conventional manner, for example with sutures 290 as illustrated, to form the anastomosis 280. Intestine 270 has intestinal or luminal wall 272, inner surface 274, outer surface 278 and intestinal lumen 276. Approximately one half of the length of the device 10 is inserted in lumen 276 superior to the anastomosis 280 with the remaining half lying inferior to the anastomosis 280.

After the initial placement in the lumen 276 of intestine 270, the device 10 is subjected to compression from the natural peristaltic action of surrounding luminal walls 272 acting through inner surface 274. As the device 10 is subjected to the surrounding peristaltic contractions, the device is compressed inwardly as illustrated in FIG. 5. Since the outer member 130 is weaker than the inner member 80, the outer member 130 collapses inwardly toward the inner member 80. The force that is exerted is transferred into any fluid located within the compartment 200 between the members 80 and 130. As the pressure increases, the one-way valve structures 94 in member 80 open inwardly allowing egress of the trapped fluid contained in volume 200 between the layers 130 and 80 into the central lumen 110 (illustrated as the arrows marked 290). The same trapped fluid volume pressure exerts a closing force on the valve members 170 contained in the outer member 130 as they are naturally a one way valve structure that closes when the pressure increases in the trapped volume in compartment 200.

Once the peristaltic contraction releases, the outer member 130 of the device 10 expands along with the luminal wall 272 of the intestine 270 as seen in FIG. 6. The inner member 80 remains relatively immobile during this relaxation. As the walls move away from each other, the pressure within compartment 200 is reduced. This reduction in pressure causes the valves 170 in the outer member 130 to open inwardly. As there is a discontinuous contact of the compaction element 40 with the surrounding walls, there is effectively a low pressure zone created near the anastomosis and within compartment 200. The negative pressure allows for the evacuation of secretions from the site of the anastomosis preferentially into the device 10 as indicated by the arrows 295 instead of toward the external regions of the anastomosis 280.

As the next wave of muscle contractions occur, the one-way valves 170 in member 130 close and the inner one-way valves 94 open, repeating the cycle as detailed previously. In this way, each contraction of the musculature causes essentially a continuous negative pressure zone on the local anastomosis with the exception of the contractile periods. During the contractile periods, the anastomosis remains protected from intestinal contents as the external valves reseal during the contractions. The pressure in the cavity 200 will vary with the peristaltic cycle from positive during contractions to negative between contractions when the device is in a resting state. The positive pressure will be sufficient to effectively expel any liquids and entrained solids from the cavity 200. For example (and not meant to be limiting), the pressure may range from about 10 to about 30 mm $H_2O$. The negative pressure will be sufficient to effectively move bodily fluids and contaminants about the exterior of device 10 into the cavity 200 and to provide a negative pressure acting upon the tissue surrounding the device 10.

If desired, the device may be optionally fabricated with an external source of negative pressure for priming at the time of surgery or to operate during the early phases of recovery when systemic narcotic pain medications are in use.

In another embodiment of the present invention, the outer functional member 120 is eliminated, and the device consists of the inner functional member 70 having one-way valves and the outer compression member 30. Such an embodiment would also have luminal sealing members 22 on both opposed ends. In another embodiment of the present invention, the one-way valves on the inner and outer functional members 70 and 120 are reversed such that flow is reversed from the interior lumen 110 to the cavity 120 to the exterior of member 120. Such a device with a reverse flow has applications in the digestive tract, for example, mounted in the stomach. The device would allow an egress of fluid containing, for example, nutrients, while protecting materials in the inner lumen, for example, drugs, from bodily fluids such as stomach acid or enzymes.

As mentioned previously, a preferred application for the protective devices of the present invention is in the lumen of an intestine proximate an anastomosis site. The devices of the present invention may be used in hollow organs including the organs of the digestive system, glands, ureters, and any hollow organ or duct where a contractile force would act upon the device. The devices may also be used in blood vessels having contractile walls such as arteries. If desired, the devices of the present invention may have utility as fluid drains when implanted adjacent to skeletal muscles, for example adjacent to an infected wound in an extremity, wherein expansion and contraction of the muscle would act upon the device to transport fluid from the infected site to the interior lumen of the device, which can be connected to a conventional drain.

The following examples are illustrative of the principles and practice of the present invention although not limited thereto.

EXAMPLE 1

An anastomosis is performed on a patient in a conventional manner using the following procedure. A bowel anastomosis is created in two layers using an absorbable monofilament suture. The affected segment of bowel is divided between clamps and the diseased segment is resected. The inner layer of sutures incorporate the full thickness of the bowel wall and an outer layer of seromuscular sutures. Stay sutures are inserted in the mesenteric and anti mesenteric borders and a posterior layer of seromuscular sutures are then inserted in an interrupted fashion. A continuous suture line is created through the use of a double ended suture applied from a center starting point, working in opposing directions, taking full thickness bites. The suture is tied in the middle of the anterior wall. The anterior wall is reinforced with inverting interrupted seromuscular sutures. The edges of the mesentery are closed to prevent any internal herniation. The patency of the anastomosis is tested prior to closure.

After the anastomosis is completed, a protective device of the present invention is inserted into the patient's intestinal lumen in the following manner. The device is loaded onto a catheter style delivery instrument with the instrument passing through the central lumen of the protective device. The proximal eyelet of the device is engaged with an anchoring feature located proximally on the delivery shaft. The eyelet located on the distal end of the protective device is engaged with the anchoring feature located on the distal end of the delivery instrument. A conventional lever style handle is squeezed to force the two eyelets apart in an axial direction. The axial motion causes the device to collapse radially. Once the device is collapsed, the protective device is inserted into the lumen to be protected and is advanced to the site of the anastomosis. The device is advanced under radiographic imaging or under optical visualization until the center portion of the device is located proximate the site of the anastomosis. The handle of the delivery device is then actuated to allow the protective device to expand radially within the lumen of the intestine. The locking features are disengaged from the eyelets of the device and delivery instrument is withdrawn from the central lumen of the protective device. No energy source or external drive is required for the passive device to operate. While in place, the device passively provides for the removal of fluids and protects the anastomosis site. Once the wound has been allowed to heal for approximately 3-7 days, the device is subsequently removed. The device is removed through the reversal of the process previously outlined for delivery, insertion of the removal instrument, engagement of the locking features with the eyelets, extension of eyelets axially, and withdrawal of the device from the lumen of the intestine. Optionally, a device constructed from bioabsorbable components is utilized in the procedure, and the device is broken down and excreted from the lumen. Such bioabsorbable components may be made from conventional bioabsorbable polymeric materials including known and available bioabsorbable polyester polymers and copolymers.

The novel anastomosis protection devices of the present invention have numerous advantages. The devices provide a means for removing exudate from an anastomosis site. This is important because edema is reduced as excess fluid is removed from the site during the healing process. The devices also protect the anastomosis site from fecal matter and digestive juices. The devices apply a negative pressure to tissue surrounding the anastomosis site which is believed to contribute to healing by attracting endothelial and mesothelial cells.

Additionally, the devices of the present invention may be utilized within the site of an arterial aneurism. The device may be placed endoluminally through a delivery catheter as previously described. The device can be sized to bridge the aneurism and engages with healthy vascular tissue both proximally and distally to the diseased portion of the artery. Unlike stent grafts where the blood contained within the dilated artery remains in place in a static condition, the valving mechanism, previously detailed, in combination with the vascular contractions, provide a means for reducing the volume of fluid trapped within the dilated portion of the vessel, potentially enabling remodeling of the diseased portion of the artery.

The devices are easy to install and remove, and perform their function in a passive manner without the need for external drives or energy sources. The devices may also reduce the incidence of hospital acquired infections.

Although this invention has been shown and described with respect to detailed embodiments thereof, it will be understood by those skilled in the art that various changes in form and detail thereof may be made without departing from the spirit and scope of the claimed invention.

I claim:

1. A medical device for protecting anastomosis sites, comprising:
    an inner tubular member having an inner lumen, a diameter, an outer surface, an inner surface, opposed ends, and a sidewall, wherein the diameter of the tubular member varies at least partly along the length of the tubular member;
    an outer tubular member having an inner lumen, a length, opposed ends, an outer surface, an inner surface, and a sidewall;
    an outer compressive member having an inner lumen;
    valves contained in the side wall of the inner tubular member;
    valves contained in the side wall of the outer tubular member,
    wherein the inner tubular member is concentrically mounted in the lumen of the outer tubular member forming a fluid-tight cavity between the inner surface of the outer member and the outer surface of the inner member;
    wherein the outer compressive member is concentrically mounted about the outer tubular member;
    wherein the inner tubular member and the outer tubular member each have a radial strength, and the radial strength of the inner tubular member is greater than the radial strength of the outer tubular member; and
    wherein a fluid pathway is formed from an exterior surface of the outer tubular member and extending through the valves in the outer tubular member wall, into the cavity, out of the cavity through the valves in the inner tubular member wall and into the inner lumen of the inner tubular member.

2. The medical device of claim 1, wherein the valves are one-way valves that open inwardly.

3. The medical device of claim 1, wherein the outer tubular member comprises an elastomeric material.

4. The medical device of claim 1, wherein the inner tubular member comprises an elastomeric material.

5. The medical device of claim 3, wherein the elastomeric material comprises a material selected from the group consisting of silicone, rubber, elastomeric thermoplastic polymeric resins, elastomeric polymeric resins, and combinations thereof.

6. The medical device of claim 4, wherein the elastomeric material comprises a material selected from the group consisting of silicone, rubber, elastomeric thermoplastic polymeric resins, elastomeric polymeric resins, and combinations thereof.

7. The medical device of claim 1, wherein the compression member comprises a helical spring having a plurality of coils and opposed ends.

8. The medical device of claim 1, wherein the compression member is selected from the group consisting of helical springs, woven structures, braided structures, central core pulley and cable assemblies, foam structures, balloon structures, and textile structures.

9. The medical device of claim 1, wherein the opposed ends of the inner tubular member are joined to the corresponding opposed ends of the outer tubular member.

10. The medical device of claim 1, wherein the valves are formed by cutting angulated slits into the sidewalls of the inner and outer tubular members.

11. The medical device of claim 1, wherein the inner tubular member, the outer tubular member and the compression member comprise biodegradable polymeric materials.

12. The medical device of claim 1, wherein the cavity comprises at least one compartment.

13. The medical device of claim 1, wherein the cavity comprises an annular cavity.

14. The device of claim 1, additionally comprising a luminal seal extending from each end of the outer tubular member.

15. The device of claim 14, wherein the luminal seal comprises a flange.

16. The device of claim 1, wherein the valves are selected from the group consisting of flap valves, ball valves, balloon valves, piston valves, and tricuspid valves.

17. The device of claim 1, wherein the pressure inside of the cavity is negative when the device is in a resting state.

18. The device of claim 1, wherein the pressure inside of the cavity is positive when the device is in a compressed state.

19. A method of protecting an anastomosis site, comprising the step of:
    inserting a protective device intraluminally into a lumen of a hollow organ at an anastomosis site, the device comprising:
    an inner tubular member having an inner lumen, a diameter, an outer surface, an inner surface, opposed ends, and a sidewall, wherein the diameter of the tubular member varies at least partly along the length of the tubular member;

an outer tubular member having an inner lumen, a length, opposed ends, an outer surface, an inner surface, and a sidewall;
an outer compressive member having an inner lumen;
valves contained in the side wall of the inner tubular member;
valves contained in the side wall of the outer tubular member,
wherein the inner tubular member is concentrically mounted in the lumen of the outer tubular member forming a fluid-tight cavity between the inner surface of the outer member and the outer surface of the inner member;
wherein the outer compressive member is concentrically mounted about the outer tubular member;
wherein the inner tubular member and the outer tubular member each have a radial strength, and the radial strength of the inner tubular member is greater than the radial strength of the outer tubular member; and
wherein a fluid pathway is formed from an exterior surface of the outer tubular member and extending through the valves in the outer tubular member wall, into the cavity, out of the cavity through the valves in the inner tubular member wall and into the inner lumen of the inner tubular member.

20. The method of claim 19, wherein the valves are one-way valves that open inwardly.

21. The method of claim 19, wherein the outer tubular member comprises an elastomeric material.

22. The method of claim 19, wherein the inner tubular member comprises an elastomeric material.

23. The method of claim 21, wherein the elastomeric material comprises a material selected from the group consisting of silicone, rubber, elastomeric thermoplastic polymeric resins, elastomeric polymeric resins, and combinations thereof.

24. The method device of claim 22, wherein the elastomeric material comprises a material selected from the group consisting of silicone, rubber, elastomeric thermoplastic polymeric resins, elastomeric polymeric resins, and combinations thereof.

25. The method of claim 19, wherein the compression member comprises a helical spring having a plurality of coils and opposed ends.

26. The method of claim 19, wherein the compression member is selected from the group consisting of helical springs, woven structures, braided structures, central core pulley and cable assemblies, foam structures, balloon structures, and textile structures.

27. The method of claim 19, wherein the opposed ends of the inner tubular member are joined to the corresponding opposed ends of the outer tubular member.

28. The method of claim 19, wherein the valves are formed by cutting angulated slits into the sidewalls of the inner and outer tubular members.

29. The method of claim 19, wherein the valves are selected from the group consisting of flap valves, ball valves, balloon valves, piston valves, and tricuspid valves.

30. The method of claim 19, wherein the pressure inside of the cavity is negative when the organ is in a resting state.

31. The method of claim 19, wherein the pressure inside of the cavity is positive when the organ is in a contracted state.

32. The method of claim 19, wherein the anastomosis site is selected from the tissues of the alimentary tract 33. The method of claim 19, wherein the organ is selected from the group consisting of the bladder, digestive system, glands, and circulatory system.

34. The method of claim 19, wherein the cavity comprises at least one compartment.

35. The method of claim 19, wherein the inner tubular member, the outer tubular member and the compression member comprise biodegradable polymeric materials.

* * * * *